United States Patent [19]

Reiff et al.

[11] Patent Number: 5,106,983

[45] Date of Patent: Apr. 21, 1992

[54] PROCESS OF MAKING CARFENTANIL AND RELATED ANALGESICS

[75] Inventors: Louis P. Reiff, Edgewood, Md.; Paul B. Sollman, Fort Myers, Fla.

[73] Assignee: The United States of America as represented by the Secretary of the Army, Washington, D.C.

[21] Appl. No.: 517,012

[22] Filed: Apr. 30, 1990

[51] Int. Cl.$^5$ .......................................... C07D 263/56
[52] U.S. Cl. .................................. 546/224; 546/223
[58] Field of Search ............................... 546/223, 229

[56] References Cited

U.S. PATENT DOCUMENTS 4,179,569 12/1979 Janssen et al. ...................... 546/223
4,246,267 1/1981 Vincent et al. ...................... 546/224

Primary Examiner—C. Warren Ivy
Assistant Examiner—Raymond Covington
Attorney, Agent, or Firm—Anthony T. Lane; Edward Goldberg; Edward F. Costigan

[57] ABSTRACT

An improved process or method of synthesis of carfentanil and other potent analgesics of the N-alkyl 4-substituted 4-piperidinylamide class which can be used as morphine substitutes.

1 Claim, No Drawings

PROCESS OF MAKING CARFENTANIL AND RELATED ANALGESICS

GOVERNMENTAL INTEREST

The invention described herein may be manufactured and licensed by or for the Government for governmental purposes without payment to us of any royalties.

FIELD OF USE

This invention relates to an improved process or method of synthesis of carfentanil and other potent analgesics of the N-alkyl 4-substituted 4-piperidinylamide class which can be used as morphine substitutes.

BACKGROUND

The compounds of interest, and their related syntheses appeared in the literature starting in 1976. However, due to the low overall yield obtained in their preparation, a great deal of improvement was desired. A synthetic route leading to analgesics of the above-cited type is described in the literature, see Synthetic Analgesics, Arzeim-Forsch. 26, 1548 (1976) and U.S. Pat. No. 4,179,569, Dec. 18, 1979. This synthesis is shown below:

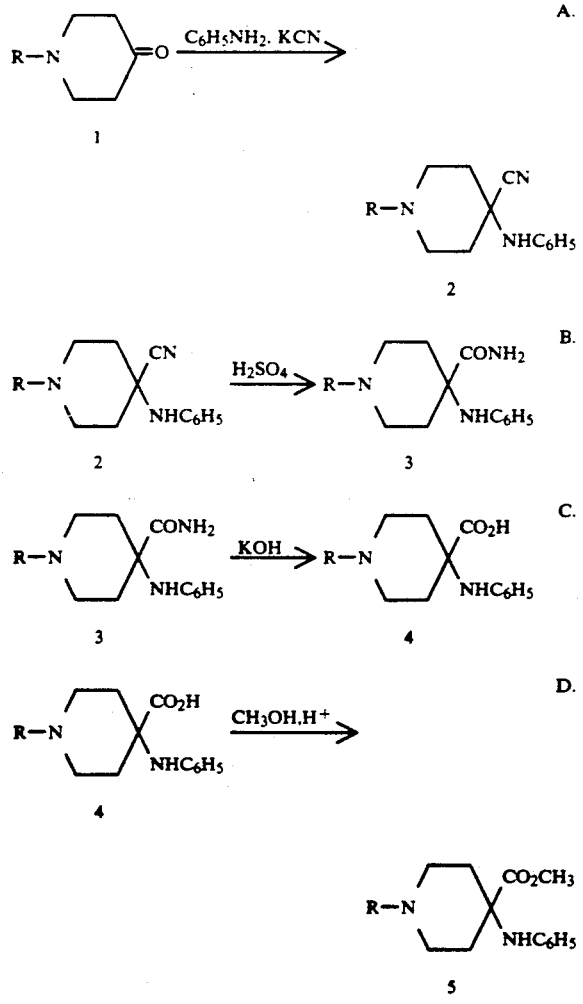

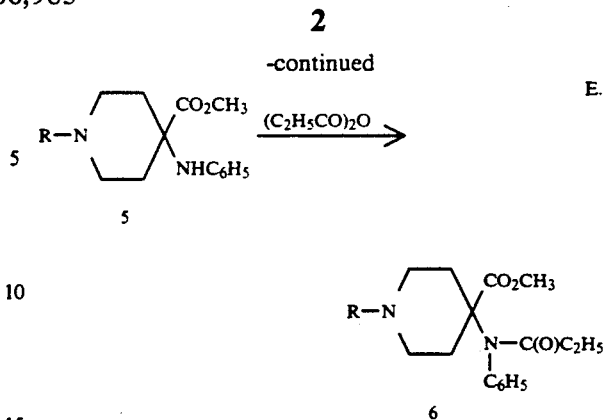

It should be noted that when R is a phenylethyl group, the product is called Carfentanil, one of the most biologically active in this series.

The reaction of 1-phenylethyl-4-piperidine (1) with KCN and aniline in acetic acid gives 4-anilino-4-cyano-1-(2-phenylethyl)piperidine (2), which is hydrolyzed with cool $H_2SO_4$ to the corresponding amide (3). This compound is hydrolyzed further with KOH in refluxing ethylene glycol affording the free acid (4), which is methylated with methanol and an acid catalyst to the methyl ester (5). Finally this compound is acylated with propionic anhydride at reflux temperature to give the analgesic compound (6).

For several N-alkyl or alkaryl groups of interest, the route described in the series of formulas gives satisfactory results. When R is phenylethyl, however, in order to prepare Carfentanil, the yield of the hydrolysis of the nitrile to the corresponding amide (Equation B) is very low (about 7% or less). The predominant reaction is the reverse of Equation A, and the main product is the ketone (1) again.

SUMMARY OF INVENTION

It is an object of this invention to provide a process or method of synthesis of Carfentanil in yield of about 47 percent, for a key step.

Using the sequence of reactions and conditions of this invention disclosure, the yield of the critical hydrolysis step (Equation B) can be substantially improved from about 7% to around 47%. This allows a more practical and efficient total synthesis; less starting materials are required and less chemical wastes are generated.

PREFERRED EMBODIMENT

This invention relates to the synthesis of Carfentanil (9) by the sequence of reactions the claims. The first reaction is again a Strecker synthesis to give an aminonitrile (2) as before. The nitrile is then converted to a formamide (7) with formic acid and acetic anhydride. This compound is hydrolyzed to an imidate (8) with refluxing methanolic hydrogen chloride. Decomposition of this in dilute base gives an amide (3), which is the same product of Equation B. The net yield for these three steps (G, H and I) which substitutes for Equation B is about 47%, whereas the yield from B is only 7%. The amide is further hydrolyzed to an acid and converted to a methyl ester by the same procedures as before (Equations C and D). Finally, the methyl ester is acylated to give Carfentanil (9). (Equation J).

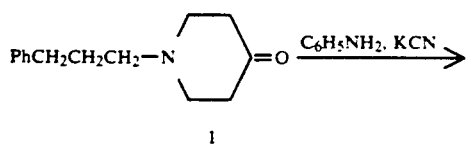

F.

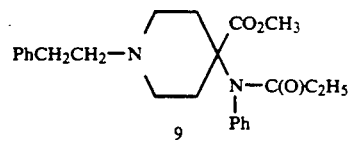

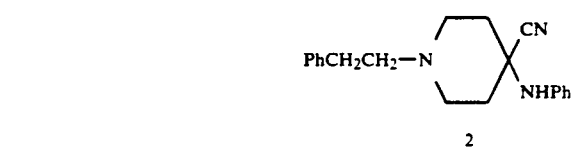

G.

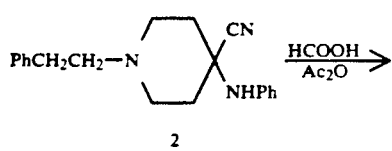

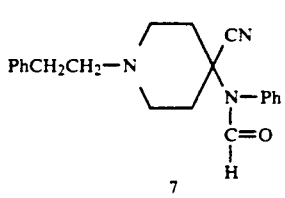

H.

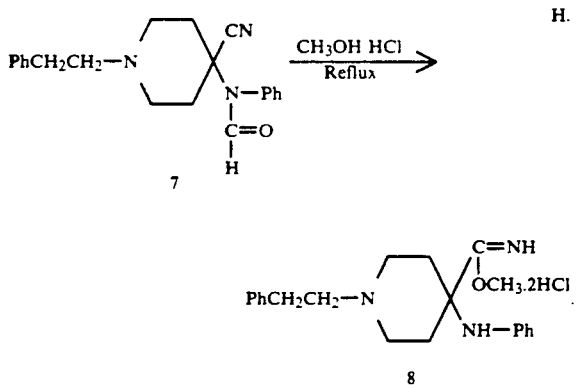

I.

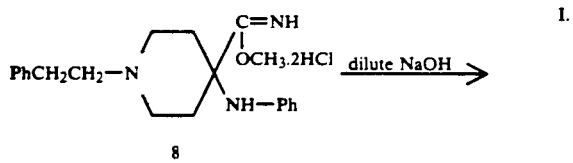

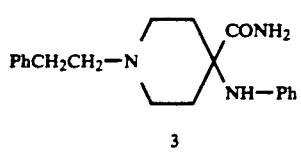

J.

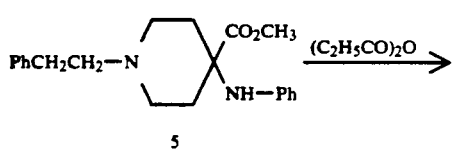

SPECIFIC EMBODIMENT OF PROCESS OF THIS INVENTION

A solution of 60.5 g (0.929 mole) of potassium cyanide in 181 mL of water was added slowly to a stirred solution of 127 g (0.625 mole) of 1-(β-phenethyl)-4-piperidone and 87.1 g (0.935 mole) of aniline in 635 mL of glacial acetic at 25°–30° C. After stirring for a total of 45 hours at room temperature, the reaction mixture was poured into a mixture of 900 g of ice and 1610 mL of concentrated ammonium hydroxide with stirring for two hours during which a brown solid precipitated out. The solid was filtered and washed with water. Recrystallization from isopropanol gave a total of 125 g (66% yield) of product, 1-(β-phenethyl)-4-(N-phenylamino)-4-piperidine carbonitrile, as tan crystals, m.p. 119°–120° C.

Formic acid (600 mL) was added to 600 mL of acetic anhydride at a rate such that the temperature of the mixture did not exceed 42° C. To this solution was added 119 g (0.39 mole) of 1-(β-phenethyl)-4-(N-phenylamino)-4-piperidine carbonitrile at 5°–10° C. with stirring. After standing at room temperature overnight, the reaction mixture was poured into ice-water and made alkaline to pH 7.4 with dilute sodium hydroxide solution during which a tan solid precipitated out. The solid was filtered and washed with water. Recrystallization from methanol gave 100.4 g (77.3% yield) of product (1-(β-phenethyl)-4-(N-formyl-N-phenylamino)-4-piperidine carbonitrile, as white crystals, m.p. 136°–138° C.

To a suspension of 100 g (0.30 mole) of 1-(β-phenethyl)-4-(N-formyl-N-phenylamino)-4-piperidine carbonitrile in 1.0 L of anhydrous methanol was added slowly a solution of 670 g (18.4 mole) of hydrogen chloride in 2.0 L of anhydrous methanol at 3°–10° C. The resulting yellow solution was refluxed two hours, and then the methanol was allowed to distill off until 1.7 L was collected over the next three hours. During this time a white solid precipitated out. The reaction mixture was cooled and filtered, yielding 79 g (64.2% yield) of product, methyl 1-(β-phenethyl)-4-(N-phenylamino)-4-piperidineimidate dihydrochloride, as white solid, m.p. 196°–198° C. (dec.).

A suspension of 79 g (0.19 mole) of methyl 1-(β-phenethyl)-4-(N-phenylamino)-4-piperidineimidate dihydrochloride in 675 ml of water was made alkaline to pH 9 with dilute sodium hydroxide solution. The solid was filtered and washed with water. The solid was dried in a vacuum desiccator to give 61.5 g (98.8% yield) of product, 1-(β-phenethyl)-4-(phenylamino)-4-piperidine carboxamide, as a white solid m.p. 181°–183° C.

A solution of 28.4 g (0.088 mole) of 1-(β-phenethyl)-4-(N-phenylamino)-4-piperidine carboxamide and 17 g of potassium hydroxide in 114 mL of ethylene glycol was allowed to reflux for 3 hours. The reaction mixture was poured into 228 mL of ice-water and made acidic to pH 6–6.5 with concentrated hydrochloric acid during which a tan solid precipitated out. The solid was filtered and washed with cold water. The solid was suspended in benzene and water was removed by azeotropic distillation. The mixture was cooled and filtered yielding 28 g (98.3% yield) of product, 1-(β-phenethyl)-4-(N-phenylamino)-4-piperidine carboxylic acid, as a white solid, m.p. 254°-255° C. (dec.).

Concentrated sulfuric acid (12 mL) was added slowly to a stirred suspension of 25.6 g (0.079 mole) of 1-(β-phenethyl)-4-(N-phenylamino)-4-piperidine carboxylic acid in 95 mL of anhydrous methanol. The resulting solution was refluxed for a total of 73 hours. The reaction mixture was cooled and poured into 1 L of ice-water, upon which a gummy brown solid precipitated out. The mixture was made basic to pH 7.4 with dilute sodium hydroxide solution and extracted with methylene chloride. The extracts were dried over magnesium sulfate and evaporated to give 21 g of crude product which was recrystallized from N-hexane to give 19.0 g (71.1% yield) of desired product, methyl 1-(β-phenethyl)-4-(N-phenylamino)-4-piperidine carboxylate, as white crystals, m.p. 92°-93° C.

A mixture of 10.0 g (0.03 mole) of methyl 1-(β-phenethyl)-4-(N-phenylamino)-4-piperidine carboxylate and 100 g (0.77 mole) of propionic anhydride was heated to reflux for 6 hours. Most of the propionic anhydride was then removed by distillation under reduced pressure. The residue was slurried in about 100 mL of ice-water and made alkaline to pH 8 with ammonium hydroxide. The mixture was extracted with chloroform and the extracts dried over magnesium sulfate and evaporated under reduced pressure. The residue, which weighed about 12 g, was dissolved in 50 mL of isopropanol and treated with a solution of 3.8 g (0.03 mole) of oxalic acid dissolved in 50 mL of isopropanol. The product was allowed to crystallize out overnight at room temperature. When filtered and dried, there was obtained 12.2 g (85% yield) of carfentanil oxalate, or methyl 1-(β-phenethyl)-4-(N-propionyl-N-phenylamino)-4-piperidine carboxylate oxalate, m.p. 183°-185° C.

In conclusion, as heretofore indicated, the process set forth in this invention provides the Carfentanil product in an amount of about 7 times that of the processes of the art.

What is claimed is:

1. An improved process of making carfentanil and related analgesics by converting in sequence:
   a. 1-(β-phenethyl)-4-piperidone to 1-(β-phenethyl)-4-(N-phenylamino)-4-piperidine carbonitrile;
   b. said 1-(β-phenethyl)-4-(N-phenylamino)-4-piperidine carbonitrile to 1-(β-phenethyl)-4-(N-formyl-N-phenylamino)-4-piperidine carbonitrile;
   c. said 1-(β-phenethyl)-4-(N-formyl-N-phenylamino)-4-piperidine carbonitrile to methyl 1-(β-phenethyl)-4-(N-phenylamino)-4-piperidineimidate dihydrochloride;
   d. said methyl 1-(β-phenethyl)-4-(N-phenylamino)-4-piperidineimidate dihydrochloride to 1-(β-phenethyl)-4-(N-phenylamino)-4-piperidine carboxamide;
   e. said 1-(β-phenethyl)-4-(N-phenylamino)-4-piperidine carboxamide to 1-(β-phenethyl)-4-(N-phenylamino)-4-piperidine carboxylic acid;
   f. said 1-(β-phenethyl)-4-(N-phenylamino)-4-piperidine carboxylic acid to methyl 1-(β-phenethyl)-4-(N-phenylamino)-4-piperidine carboxylate; and
   g. said methyl 1-(β-phenethyl)-4-(N-phenylamino)-4-piperidine carboxylate to methyl 1-(β-phenethyl)-4-(N-propionyl-N-phenylamino)-4-piperidine carboxylate oxalate.

* * * * *